United States Patent [19]

Coronelli et al.

[11] 4,239,751

[45] Dec. 16, 1980

[54] ANTIBIOTIC SUBSTANCES

[75] Inventors: Carolina Coronelli; Grazia Beretta; Maria R. Bardone; Francesco Parenti, all of Milan, Italy

[73] Assignee: Gruppo Lepetit S.p.A., Milan, Italy

[21] Appl. No.: 30,492

[22] Filed: Apr. 16, 1979

Related U.S. Application Data

[63] Continuation of Ser. No. 847,641, Nov. 1, 1977, abandoned, which is a continuation of Ser. No. 661,910, Feb. 27, 1976, abandoned.

[30] Foreign Application Priority Data

Mar. 5, 1975 [GB] United Kingdom ............... 9057/75

[51] Int. Cl.² ............................................. A61K 35/00
[52] U.S. Cl. .................................. 424/118; 424/120; 435/169
[58] Field of Search ................ 424/118, 120; 435/169

[56] References Cited

U.S. PATENT DOCUMENTS 3,824,305  7/1974  Hamill et al. ..................... 424/118

*Primary Examiner*—Jerome D. Goldberg

[57] ABSTRACT

This invention relates to a novel antibiotic mixture and to the process for its production. This antibiotic mixture comprises a family of new antibiotic substances which may be separated and isolated as individual components.

These antibiotic substances are referred to herein as antibiotic 8327 factor A, antibiotic 8327 factor B and antibiotic 8327 factor C.

Antibiotic 8327 factor A is in turn a mixture of three fractions which will be referred to herein as teichomycin $A_1$, teichomycin $A_2$ and teichomycin $A_3$. The novel antibiotic mixture is obtained by cultivation of strain *Actinoplanes teichomyceticus nov. sp.* ATCC 31121.

7 Claims, 3 Drawing Figures

ANTIBIOTIC SUBSTANCES

CROSS-REFERENCE TO RELATED APPLICATION

This application is a continuation of our co-pending application Ser. No. 847,641 filed Nov. 1, 1977, now abandoned, which was a continuation of copending application Ser. No. 661,910 filed Feb. 27, 1976, now abandoned.

SUMMARY OF THE INVENTION

The new antibiotics mixture and the individual factors are obtained by fermentation of a strain belonging to the genus Actinoplanes named *Actinoplanes teichomyceticus nov. sp.* and identified with our internal code A/8327. The strain has been deposited and made part of the stock culture collection of ATCC where it was assigned the number 31121.

In preparation of the novel antibiotics mixture, *Actinoplanes teichomyceticus nov. sp.* ATCC 31121 is cultivated under aerobic conditions in an aqueous nutrient medium which is suitable for the growth of said organism. The medium contains an assimilable source of carbon, an assimilable source of nitrogen and inorganic salts. Ordinarily, the antibiotic-producing strain is precultured in a shake flask until substantial mycelial growth is present, then the culture is used to inoculate jar fermentors containing nutrient fermentative medium. Cultivation is continued, preferably at a temperature between about 25° C. and about 35° C., under aerobic conditions for a time sufficient to produce a substantial antibiotic activity, preferably from about 72 to about 120 hours. During this time, microbiological assays are carried out by the agar diffusion method to control the concentration of the antibiotic substance produced. The fermentation broth is filtered in order to separate the mycelial cake. The antibiotics mixture is isolated from the filtered fermentation broth by conventional procedures, such as, for example, by extraction with an organic solvent in which the antibiotic mixture is soluble and which is immiscible with the aqueous medium. The extraction is carried out after adjustment of the pH of the fermentation broth to about 3.5. Suitable organic solvents for the extraction are advantageously selected from halogenated $C_1$-$C_4$ hydrocarbons and $C_4$-$C_6$ alkanols. The solvent is then separated from the fermentation broth by high-speed centrifugation, concentrated to about 1/10-1/20 of its original volume, cooled and allowed to stand until a precipitate forms which is recovered on filter.

This precipitate essentially consists of antibiotic 8327 factor A (hereinafter alternatively referred to as teichomycin), which is a mixture of teichomycin $A_1$, teichomycin $A_2$ and teichomycin $A_3$. Antibiotic 8327 factors B and C essentially remain in the organic solution and are precipitated by addition of a large amount of an inert non-polar solvent such as, for example, a light petroleum.

Teichomycin $A_1$, teichomycin $A_2$ and teichomycin $A_3$ are separated from each other by column chromatography while antibiotic 8327 factors B and C are separated from each other by means of counter current distribution techniques. Additional product may be recovered by extracting the mycelial cake with aqueous acetone. After distillation of the acetone, the aqueous phase is submitted to the same treatment described above for the filtered fermentation broth.

DESCRIPTION OF THE PREFERRED EMBODIMENTS

Figure 1:
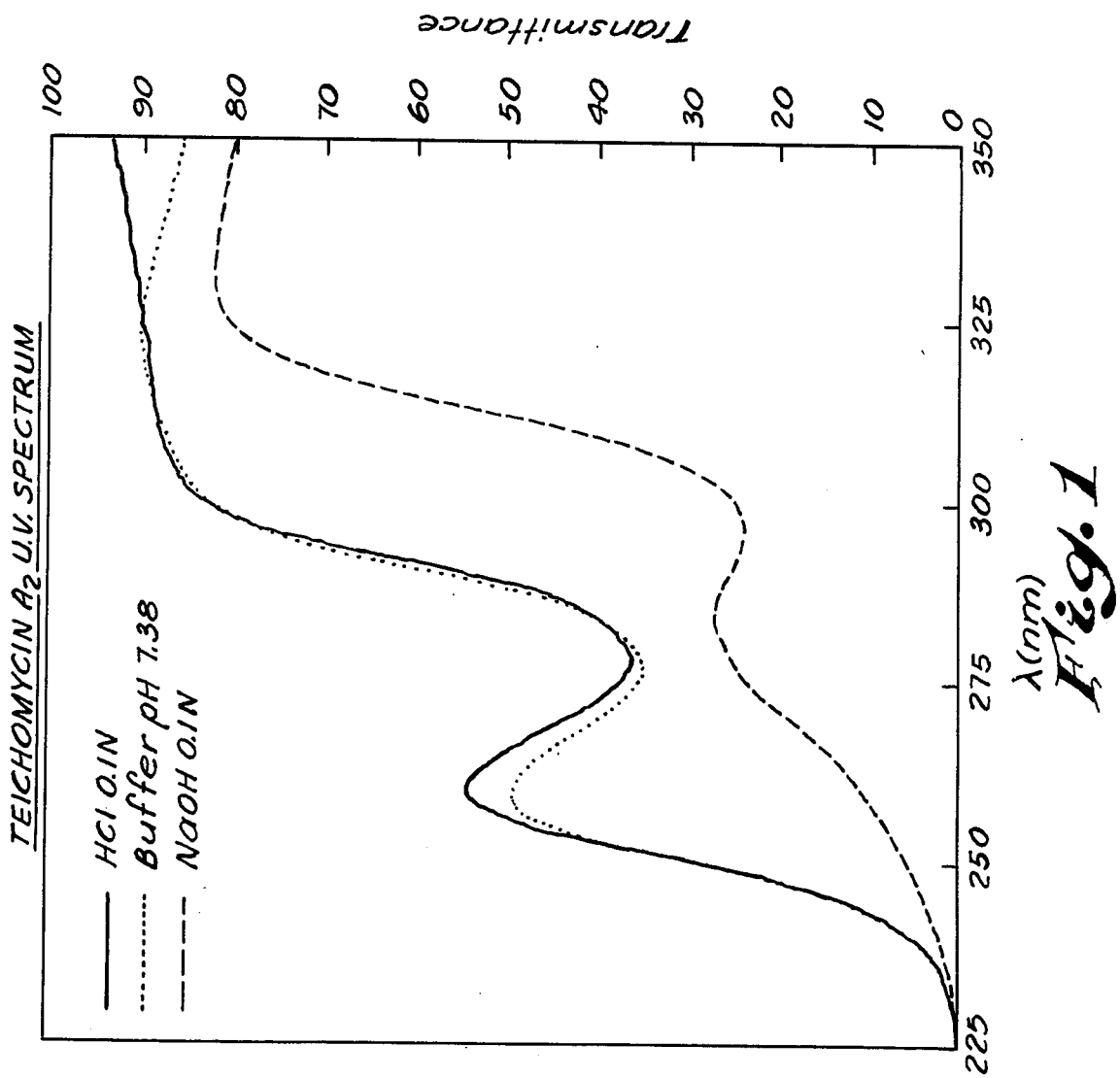

Description of *Actinoplanes Teichomyceticus nov. sp.* ATCC 31121

Macroscopic Examination of Colonies

The strain *Actinoplanes teichomyceticus nov. sp.* ATCC 31121 was isolated from a soil sample collected at Nimodi Village, Indore (India). The strain grows well on various nutrient agars. In oatmeal agar, the colonies are approximately 5 to 6 mm in diameter, show regular contours and a central dome-like protuberance. An abundant sterile aerial mycelium is found on some media.

Microscopic Examination

Sporangia are abundantly produced on most media and are mainly found on the dome of the colony. They are spherical to oval in shape, have regular contours and a diameter ranging from about 15 to about 25 m$\mu$. Sporangiospores are straight, about 15 m$\mu$ long with a diameter of about 2 m$\mu$. The spores are highly motile and are spherical to oval with a diameter of about 1.5-2 m$\mu$.

Table I reports the cultural characteristics of *Actinoplanes teichomyceticus nov. sp.* ATCC 31121 cultivated on various standard media suggested by Shirling and Gottlieb (*Int. J. Syst. Bacteriol.*, 16, 313–340, 1966) and other media recommended by Waksman (*The Actinomycetes*, Vol. II, The Williams and Wilkins Co., 1961). The cultural characteristics were determined after 6–14 days of incubation at 30° C.

Table II reports the utilization of carbon sources examined according to the method of Pridham and Gottlieb (*Journal Bacteriol.*, 56, 197, 1948).

Table III reports the physiological characteristics of the strain.

The strain *Actinoplanes teichomyceticus nov. sp.* ATCC 31121 has been cultured concomitantly with: *A. brasiliensis, A. missourensis, A. uthaensis, A. filippinensis, A. italicus, A. armeniacus, A. deccanensis* ATCC 21983, *A. garbadinensis* ATCC 31049, and *A. liguriae* ATCC 31048. It could be clearly distinguished from all these species on the basis of morphological and pigmentation characteristics. In addition, it peptonizes litmus milk, an infrequent feature shared with the cherry-rose pigmented *A. italicus.*

TABLE 1

| CULTURE MEDIUM | CULTURAL CHARACTERISTICS |
|---|---|
| | CULTURAL CHARACTERISTICS |
| Hickey and Tresner's agar | Abundant growth with smooth surface, light brown 14/B/9 - Traces of whitish aerial mycelium - Moderate production of sporangia - Brown soluble pigment. |
| Bennett's agar | Abundant growth with smooth surface, light orange 9/B/7 - Moderate production of pale pink aerial mycelium |
| Czapek glucose agar | Abundant growth with smooth surface, light orange 9/H/7 - Produc- |

TABLE 1-continued

| CULTURE MEDIUM | CULTURAL CHARACTERISTICS |
|---|---|
| | tion of white-rose aerial mycelium - Some sparse sporangia |
| Czapek sucrose agar | Abundant growth with smooth surface, pale orange 9/B/7 - Moderate production of sporangia |
| Glucose asparagine agar | Moderate growth with smooth surface, orange 10/D/12 |
| Potato agar | Abundant growth with smooth and thin surface, light hazel-brown - Abundant production of light pink sporangia - Light hazel-brown soluble pigment |
| Nutrient agar | Poor growth with smooth and thin surface, orange 10/5/11 |
| Egg albumin agar | Abundant growth with smooth surface, light pinkish orange 9/B/5 - Abundant production of sporangia |
| Peptone-glucose agar | Abundant growth with wrinkled surface, deep orange 10/C/12 - Light amber soluble pigment |
| Potato plug | Poor growth with wrinkled surface, light orange |
| Loeffler blood serum | Some sparse colony, light orange with grayish brown - soluble pigment |
| Medium No. 2 (Yeast extract-malt agar) | Abundant growth with slightly wrinkled surface, light pinkish orange 9/B/6 - Abundant sporangia, light pink 9/A/5 - Amber soluble pigment |
| Medium No. 3 (Oatmeal agar 20%) | Abundant growth with smooth surface, pale orange 9/B/5 - Abundant sporangia, light pink 9/A/5 |
| Medium No. 4 (Starch agar) | Abundant growth with smooth surface, deep orange 9/H/10 - Scarce production of sporangia |
| Medium No. 5 (Glycerol-asparagine agar) | Abundant growth with thin and smooth surface, pale orange 9/B/7 - Moderate production of aerial mycelium, light pink |
| Medium No. 6 (Peptone-yeast extract iron agar) | Scarce growth |
| Medium No. 7 (Tyrosine agar) | Moderate growth with smooth and thin surface, pinkish brown 12/A/9 - Production of scant and whitish aerial mycelium - Pinkish-brown soluble pigment 12/A/9 |
| Oatmeal agar (60%) | Abundant growth with smooth surface, pale orange 9/B/5 to light orange brown 12/B/8 with the age - Abundant sporangia, light pink 9/B/5, light hazel-brown soluble pigment |
| Skim milk agar | Abundant growth with smooth surface, burnt amber 15/A/12 - Deep amber brown soluble pigment 7/E/12 |
| Calcium-malate agar | Poor growth with smooth and thin surface, pale orange 9/B/5 - Moderate production of sporangia |
| Agar | Moderate growth, colorless - Abundant formation of sporangia |
| Gelatin | Amber soluble pigment |
| Nitrate broth | Amber soluble pigment |

Color determination was made by the method of Maerz and Paul (Maerz. A. and Paul, M., *A Dictionary of Color*, 2nd ed., (1950) McGraw-Hill, New York).

The numbers given in Table I to the culture media are given according to the method of Shirling and Gottlieb, op. cit.

TABLE II
CARBON UTILIZATION

| Carbon Source | Growth |
|---|---|
| Inositol | 0 |
| Fructose | 2 |
| Rhamnose | 0 |
| Mannitol | 2 |
| Xylose | 2 |
| Raffinose | 0 |
| Arabinose | 2 |
| Cellulose | 0 |
| Salicin | 1 |
| Sucrose | 2 |
| Mannose | 2 |
| Lactose | 1 |
| Glucose (positive control) | 2 |

0 = no utilization
1 = doubtful utilization
2 = strongly positive utilization

TABLE III
PHYSIOLOGICAL CHARACTERISTICS

| Tests | Results |
|---|---|
| Starch hydrolysis | ++ |
| H$_2$S formation | ++ |
| Chromogenic action | ++ |
| Tyrosine hydrolysis | − |
| Casein hydrolysis | +++ |
| Ca-malate hydrolysis | − |
| Lytmus milk coagulation | − |
| Lytmus milk peptonization | + |
| Nitrate reduction | ++ |
| Gelatin liquefaction | ++ |
| Cellulose decomposition | − |

− = negative response
+ = weak positive response
++ = positive response
+++ = strong positive response

Production of the Antiobiotics and Isolation

For producing the antibiotic substances, the strain *Actinoplanes teichomyceticus* nov. sp. ATCC 31121 is aerobically pre-cultured in a nutrient medium until substantial mycelial growth is present, at a pH value ranging from about 6 to about 8.

As an example of the nutrient medium, a shake flask culture may have the following composition in g/l.

| | |
|---|---|
| Meat extract | 3.0 |
| Tryptone | 5.0 |
| Yeast extract | 5.0 |

-continued

| | |
|---|---|
| Glucose | 1.0 |
| Soluble starch | 24.0 |
| Calcium malate | 4.0 |
| Distilled water q.s. to | 1000 ml. |

The flasks are shaken for about 24 hours at about 28°-30° C. and then the pre-cultures (one liter) are used to inoculate jar fermentors, each containing 10 liters of the following nutrient medium:

| | |
|---|---|
| Meat extract | 40 g. |
| Peptone | 40 g. |
| Yeast extract | 10 g. |
| Sodium chloride | 25 g. |
| Soybean meal | 100 g. |
| Glucose | 500 g. |
| Calcium carbonate | 50 g. |
| Tap water q.s. to | 10 liters |

The fermentation batches are incubated aerobically under stirring at 28°-30° C. At intervals, the antibiotic activity is assayed microbiologically by the standard agar diffusion method using *Staphylococcus aureus* as the test organism. The maximum activity is reached after 72-96 hours of fermentation.

Isolation of Teichomycins $A_1$, $A_2$ and $A_3$ and Antibiotic 8327 Factors B and C The antibiotics present both in the filtered medium and in the mycelial cake can be extracted with organic solvents by conventional procedures.

The filtered medium is adjusted at pH 3.5 by the addition of 8% HCl and then extracted twice with 30% butanol. The organic extracts are concentrated under vacuum at 45° C. to 1/10 of their original volume, washed with a small quantity of water at pH 3.5 and concentrated again to a small volume. The concentrated solution is allowed to stand at low temperature for 10-15 hours until a precipitate forms which is recovered by filtration. The filtered solution is poured in a large amount of light petroleum and the crude precipitate obtained recovered by filtration.

The mycelial cake is washed with water at pH 3.5, dried under vacuum and extracted with a 1 to 4 mixture of water to acetone. The acetonic extract is concentrated under vacuum at 40°-45° C. The aqueous residue is adjusted to pH 3.5 and extracted three times with butanol. The collected butanolic extracts are washed with a small quantity of water at pH 3.5 and concentrated under vacuum to 1/20 of their original volume. The concentrated solution is allowed to stand at 4° C. for 10-12 hours. A crude precipitate is obtained which is collected by filtration. The filtered solution is poured in a large amount of light petroleum to give a further precipitate.

Chromatographic investigation carried out as indicated in Table IV shows that the products obtained by cooling the concentrated butanolic extracts contain essentially teichomycin $A_1$, teichomycin $A_2$ and teichomycin $A_3$. Teichomycin $A_2$ is the fraction present in the largest amount. The products obtained by precipitation into an inert non-polar solvent, such as, for example, light petroleum, contain antibiotic 8327 factors B and C.

Antibiotic 8327 factors B and C are separated from each other by employing counter current distribution techniques and isolated as individual antibiotic compounds. A solvent system useful for the separation is a mixture of phosphate buffer M/15 pH 7,0-n-butanol-hexane 1:1:0.05.

Teichomycin $A_1$, teichomycin $A_2$ and teichomycin $A_3$ are separated from each other by column chromatography on Sephadex LH-20, which is a hydroxypropyl derivation of a cross-linked polydextran gel with an exclusion limit at about molecular weight 4,000 and a dry bead diameter of between 25 and 100 microns, using a mixture of n-propanol:ethyl acetate:$NH_4OH$ 0.2 N 10:7:7 as eluent.

The separately eluted fractions are analyzed with silica gel TLC and using n-propanol:ethyl acetate:concentrated $NH_4OH$ 2:1:2 as solvent system and microbiological development on *S. aureus* as detecting system. Teichomycin $A_1$ has Rf=0.48; teichomycin $A_2$ Rf=0.10 and teichomycin $A_3$ Rf=0.0.

The separate antibiotic fractions containing, individually, teichomycin $A_1$, teichomycin $A_2$ and teichomycin $A_3$ are each concentrated to a very small volume, diluted with methanol and poured in a large volume of acetone. Teichomycin $A_1$, teichomycin $A_2$ and teichomycin $A_3$ will each precipitate as a whitish amorphous powder.

The different chromatographic patterns of the five antibiotics, i.e., antibiotic 8327 factor B and factor C, teichomycin $A_1$, teichomycin $A_2$ and teichomycin $A_3$ in the various eluting systems are reported in Table IV. The chromatography was on Whatman Paper No. 1, a cotton fibre cellulose filter paper with the following characteristics: weight 85-95 g/$m^2$; thickness 0.16 mm; ash content 0.06-0.07%.

TABLE IV

Chromatographic Patterns of Antibiotic 8327 Factor B, Factor C, Teichomycin $A_1$, Teichomycin $A_2$ and Teichomycin $A_3$

| Chromatography on Whatman Paper No. 1, Visualization of the spots by microbiological development on *Staphylococcus aureus* | Factor B | Factor C | Teichomycin $A_1$ | Teichomycin $A_2$ | Teichomycin $A_3$ |
|---|---|---|---|---|---|
| ELUTING SYSTEM | | | | | |
| (1) Butanol saturated with phosphate buffer M/15 pH 6.0 | 0.85 | 0.86 | 0.0 | 0.0 | 0.0 |
| (2) Butanol saturated with water containing 2% of p-toluenesulfonic acid | 0.83 | 0.88 | 0.05 | 0.13 | 0.0 |
| (3) Butanol saturated with water containing 2% ammonium hydroxide | 0.73 | 0.79 | 0.0 | 0.0 | 0.33 |
| (4) Phosphate buffer M/15 pH 6.0 saturated with butanol | 0.0 | 0.76 | 0.20 | 0.25 | 0.65 |
| (5) 20% Aqueous solution of $NH_4Cl$ | 0.0 | — | 0.0 | 0.0 | 0.61 |
| (6) Butanol:methanol:water (40:10:20) with 0.75% of methyl orange | 0.88 | 0.88 | 0.42 | 0.37 | 0.13 |
| (7) Butanol:methanol:water (40:10:20) | 0.89 | 0.90 | 0.46 | 0.41 | 0.20 |
| (8) Ethyl acetate saturated with water | 0.20 | 0.70 | 0.0 | 0.0 | 0.0 |

TABLE IV-continued
Chromatographic Patterns of Antibiotic 8327 Factor B, Factor C, Teichomycin A₁, Teichomycin A₂ and Teichomycin A₃

Chromatography on Whatman Paper No. 1,
Visualization of the spots by microbiological development on *Staphylococcus aureus*

| | Factor B | Factor C | Teichomycin $A_1$ | Teichomycin $A_2$ | Teichomycin $A_3$ |
|---|---|---|---|---|---|
| (9) n-propanol:n-butanol:NH₄OH 10 N (2:3:4) | — | 0.88 | 0.55 | 0.43 | 0.10 |
| Thin-layer chromatography on silica gel | | | | | |
| ELUTING SYSTEM | | | | | |
| n-propanol:ethyl acetate:conc. NH₄OH (2:1:2) | — | — | 0.48 | 0.10 | 0.0 |

Biological Properties of Teichomycin $A_1$, $A_2$, $A_3$ and Antibiotic 8327 Factors B and C
(1) IN VITRO ACTIVITY

| | Minimal Inhibitory Concentration (μg/ml) | | | | |
|---|---|---|---|---|---|
| Strain | Teichomycin $A_1$ | Teichomycin $A_2$ | Teichomycin $A_3$ | 8327 Factor B | 8327 Factor C |
| *Staphylococcus aureus* ATCC 6538 | 0.02 | 0.5 | 2.0 | 2.0 | 2.0 |
| *Staphylococcus aureus* Tour | 0.05 | 1.0 | 2.0 | 5.0 | 2.0 |
| *Staphylococcus aureus* Tour + 30% bovine serum | 50 | 1.0 | 2.0 | 20 | 2.0 |
| *Streptococcus haemolyticus* C-203 | 0.5 | 0.05 | 1.0 | 2.0 | 0.5 |
| *Diplococcus pneumoniae* UC 41 | 0.5 | 0.1 | 2.0 | 2.0 | 2.0 |
| *Clostridium perfringens* ISS 30543 | 2.0 | 0.05 | 5.0 | 10 | 50 |
| *Escherichia coli* SKF 12140 | 10 | >100 | >100 | >100 | >100 |
| *Proteus vulgaris* X 19 H | 20 | >100 | >100 | >100 | >100 |
| *Pseudomonas aeruginosa* ATCC 10145 | 100 | >100 | >100 | >100 | >100 |
| *Candida albicans* SKF 2270 | >100 | >100 | >100 | >100 | >100 |
| *Trichophyton mentagrophytes* SKF 17410 | >100 | >100 | >100 | >100 | >100 |
| *Mycobacterium tuberculosis* $H_{37}R_v$ ATCC 9360 | >100 | >100 | N.D. | >100 | 100 |
| *Mycoplasma gallisepticum* H 21 C.Z.B. | N.D. | >100 | >100 | >100 | >100 |
| *Neisseria gonorrheae* | 10 | 1.0 | 10 | N.D. | 10 |

(2) Acute toxicity in mice

Teichomycin $A_1$
500 mg/kg. (i.v.)
Teichomycin $A_2$
1000 mg/kg. (i.p.)

(3) In vivo activity in experimental infections in mice

| | $ED_{50}$ mg/kg. s.c. | |
|---|---|---|
| Infection Strain | Teichomycin $A_1$ | Teichomycin $A_2$ |
| *Streptococcus haemoliticus* | 2.14 | 0.1 |
| *Staphylococcus aureus* | — | 3.97 |
| *Diplococcus pneumoniae* | 11.5 | 0.57 |

N.D. = Not Determined

8327 Factor B and 8327 factor C did not show any in vivo activity up to 80 mg/kg. s.c.

Teichomycins $A_1$, $A_2$ and $A_3$ are also active against bacteria which are resistant to widely-used antibiotics such as penicillin, tetracyclin, streptomycin, bacitracin, cephalosporin, rifampicin, streptomycin, neomycin and chloramphenicol.

Accordingly, the present invention provides a therapeutic composition comprising a novel antibiotic of the invention together with a pharmaceutically-acceptable carrier.

From the above properties, it is apparent that the new antibiotic substances may be useful for different purposes such as controlling infection diseases in animals, disinfection of objects and instruments, growth promoting agents in animals and many other uses which involve suppression of pathogenic bacteria.

When utilized as a disinfectant, the novel antibiotics of the present invention or compositions containing the same can be applied to bacterial pests or their habitats in microbiocidal amounts to obtain excellent control and kill of many organisms.

This is not to suggest that the novel antibiotics and mixtures thereof with usual additives are equally effective against all such organisms at the same concentration. For such uses, the novel antibiotics can be employed in an unmodified form or dispersed on a finely-divided solid and employed as a dust. Such mixtures can also be dispersed in water with the aid of a surface-active agent and the resulting emulsion employed as a spray. In other procedures, the novel antibiotics can be employed as the active constituents in solvent solutions, oil-in-water or water-in-oil emulsions. The augmented compositions are adapted to be formulated as concentrates and subsequently diluted with additional liquid or solid adjuvants to produce the ultimate treating compositions. Good results are obtained when employing compositions containing antimicrobial concentrations containing from about 0.5 to about 500 parts by weight of one or more of the novel antibiotics per million parts of such compositions.

Chemico-Physical Properties of Teichomycin $A_2$

Teichomycin $A_2$, obtained according to the procedures as described herein, is an amorphous powder which after further purification by treatment with a cross-linked sulfonated divinylbenzene styrene copolymer cation exchange resin (Dowex 50) in an aqueous solution to pH 4 shows the following chemico-physical properties:

(1) Melting point: 260° C. (with decomposition);

(2) Elemental analysis: The following percentage composition is the average of three different analyses: C=54.20%; H=5.70%; N=6.80%; Cl=3.30%; O (by difference)=30%;

(3) Ultraviolet absorption spectrum (see FIG. 1):

| Solvent | $\lambda_{max}$ (nm) | $E^{1\%}_{1cm.}$ |
|---|---|---|
| phosphate buffer pH 7.38 | 278 | 55 |
| hydrochloric acid 0.1 N | 278 | 53 |
| sodium hydroxide 0.1 N | 297 | 74; |

The U.V. spectrum was recorded with a Beckman DK-2 apparatus.

Figure 2:
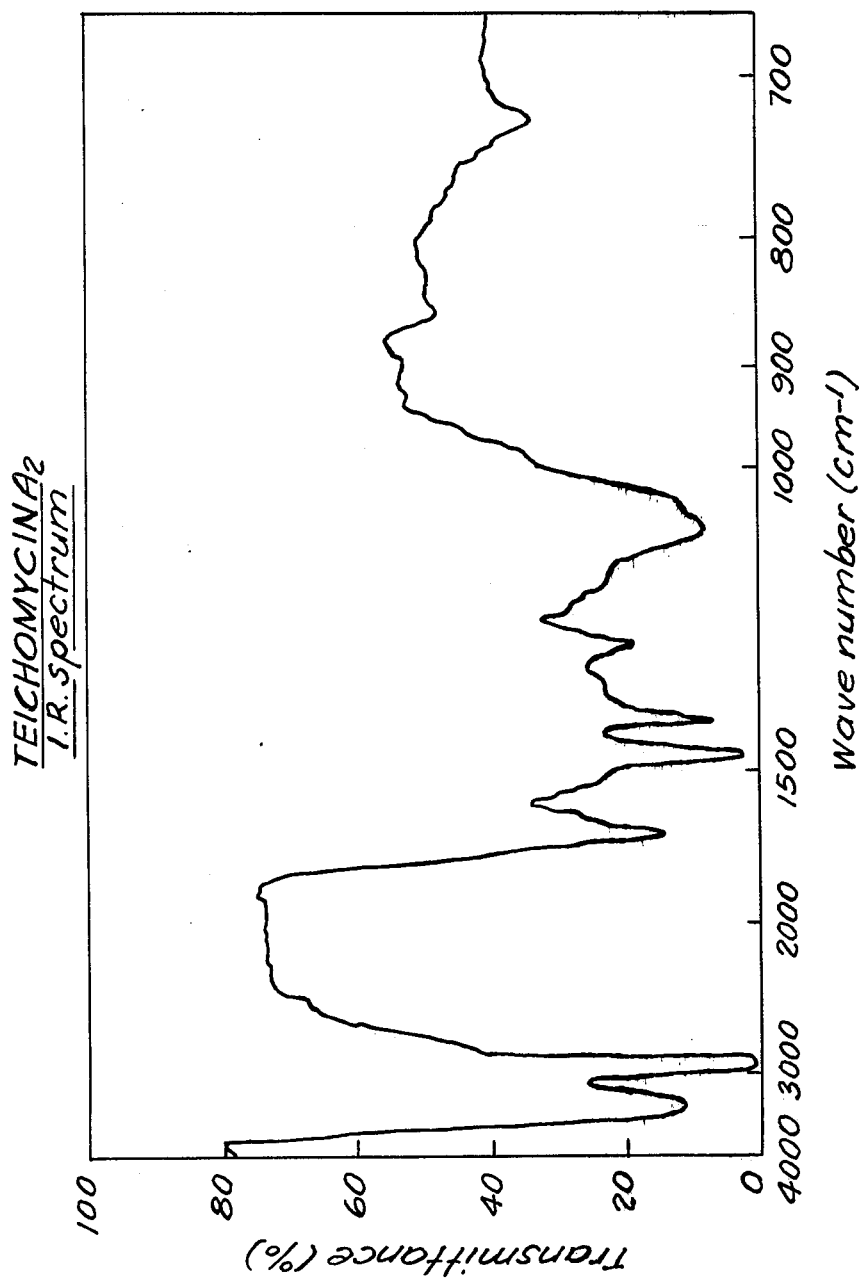

(4) I.R. absorption spectrum: The complete picture of the spectrum in nujol mull is given in FIG. 2. The most important absorption bands occur at the following frequencies (cm$^{-1}$): 3300 (broad), ~2900 (nujol), 1720 (shoulder), 1660, 1600 (shoulder), ~1500, 1455 (nujol), 1375 (nujol), 1235, 1190–930, 850, 720 (broad). The I.R. spectrum was recorded with a Perkin Elmer 157 apparatus.

(5) Solubility: soluble in aqueous solution at pH 7.0, aqueous sodium bicarbonate, diluted aqueous solutions of alkali hydroxides, methanol-water mixtures; partially soluble in methanol and ethanol; insoluble in diluted mineral acids and in non-polar organic solvents;

(6) Characteristic reactions:

| Fehling | positive |
|---|---|
| Tollens | positive |
| KMnO$_4$ | positive |
| FeCl$_3$ | positive |
| H$_2$SO$_4$ concentrated | dark violet color |
| Folin Ciocolteu | positive |
| Griess | negative |
| Antrone | negative |
| Schiff | negative; |

(7) Potentiometric titrations: An ionizable function is potentiometrically evidenced in water solutions with a pKa value=4.9; a basic function is evidenced by titration with HClO$_4$ in dimethylsulfoxide (DMSO) solutions; the equivalent weight determined accordingly is 1170.

Chemico-Physical Properties of Teichomycin $A_1$

Teichomycin $A_1$, obtained according to the procedures herein, is further purified by column chromatography on silica gel-celite (1:1 v/v) using a mixture of n-butanol:acetic acid:water (8:2:2) as eluent. It is an amorphous powder with the following chemico-physical properties:

(1) Melting point: 220° C. (with decomposition);

(2) Elemental analysis: The following percentage composition is in the average of three different analyses:

C=59.9%; H=7.6%; N=5.26%; O=32.5%; P=0.96%; ash=2.30%;

(3) Ultraviolet absorption spectrum: No absorption between 220 and 360 nm. The U.V. spectrum was recorded with a Beckman DK-2 apparatus.

Figure 3:
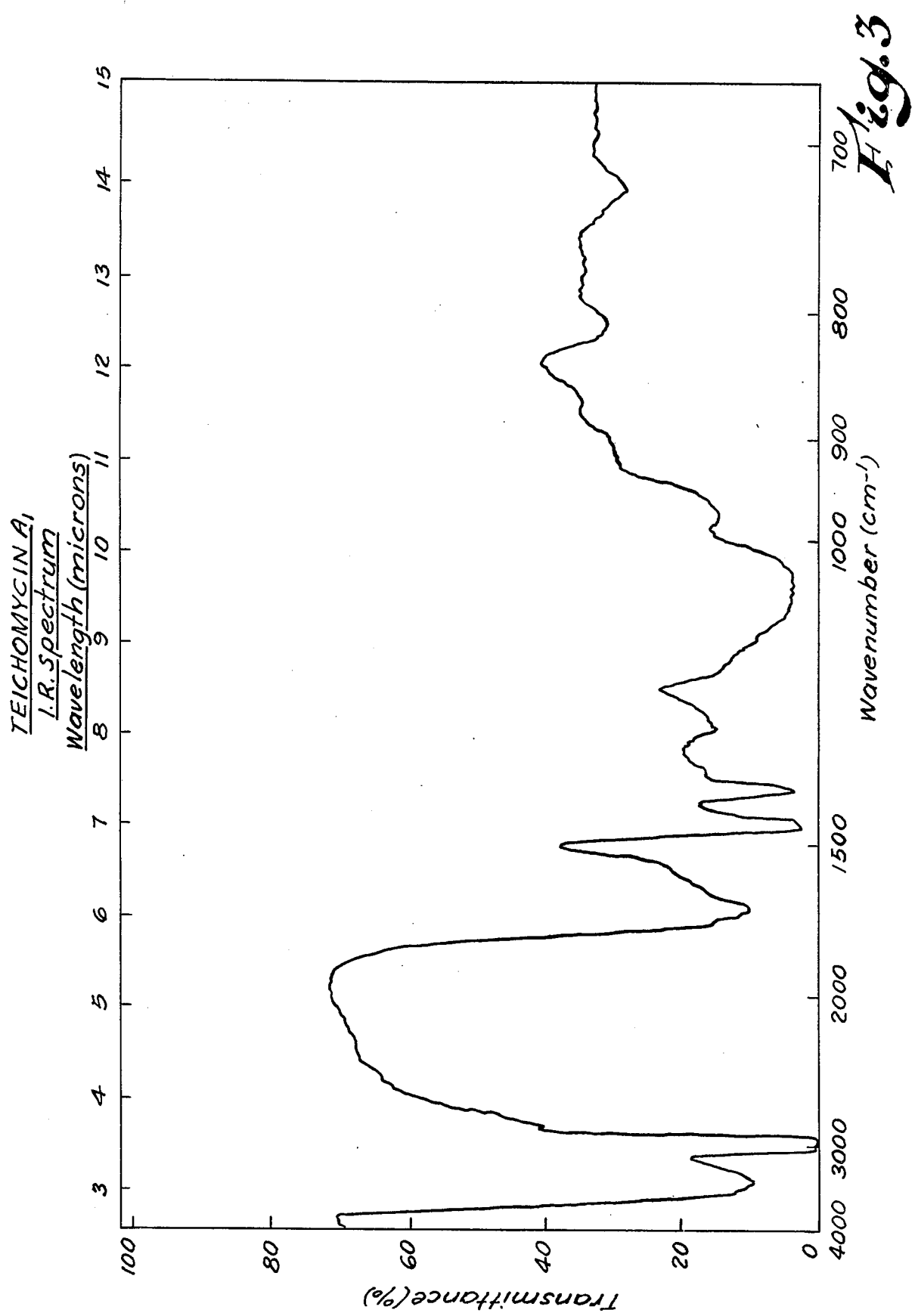

(4) I.R. absorption spectrum: The complete picture of the spectrum in nujol mull is given in FIG. 3. The mose important absorption bands occur at the following frequencies (cm$^{-1}$): 3350 (broad), 2930–2850 (nujol), 2750–2000, 1720 (shoulder), 1670 (broad), 1620 (shoulder), 1560 (broad), 1460 and 1370 (nujol), 1340 (shoulder) 1260, 1240, 1155 (shoulder), 1120 (shoulder), 1040 (very broad), 970 (broad), 950 (shoulder), 900 (broad) 865, 805, 720. The I.R. spectrum was recorded with a Perkin Elmer 517 apparatus.

(5) Solubility: soluble in aqueous solution at pH 7.0, aqueous sodium bicarbonate, diluted aqueous solutions of alkali hydroxides, dimethylformamide, dimethylsulfoxide; partially soluble in methanol and ethanol; insoluble in diluted mineral acids and in non-polar organic solvents;

(6) Characteristic reactions:

| Fehling | positive |
|---|---|
| Tollens | positive |
| KMnO$_4$ | positive |
| Griess | negative |
| Antrone | positive |
| Schiff | negative |
| Molish | positive; |

(7) Molecular weight: Determinations of molecular weight by chromatography through Sephadex G 75, a cross-linked polydextran gel with a range of fractionation, expressed in molecular weight, between 3,000 and 70,000 and a dry bead diameter of between 40 and 120 microns, show the following values: 20,000 in phosphate buffer pH 7.38, 30,000 in citrate buffer pH 4.4.

What is claimed is:

1. The antibiotic substance named teichomycin $A_2$ having the following characteristics:

(1) Melting point: 260° C. (with decomposition);

(2) Elemental analysis (average of three determinations): C=54.20%; H=5.70%; N=6.80%; Cl=3.30%; O (by difference)=30%;

(3) Ultraviolet absorption spectrum (FIG. 1):

| Solvent | $\lambda_{max}$ (nm) | $E^{1\%}_{1cm.}$ |
|---|---|---|
| phosphate buffer pH 7.38 | 278 | 55 |
| hydrochloric acid 0.1 N | 278 | 53 |
| sodium hydroxide 0.1 N | 297 | 74; |

(4) I.R. absorption spectrum in nujol mull (FIG. 2): The most important absorption bands occur at the following frequencies (cm$^{-1}$): 3300 (broad), ~2900 (nujol), 1720 (shoulder), 1660, 1600 (shoulder), ~1500, 1455 (nujol), 1375 (nujol), 1235, 1190–930, 850, 720 (broad);

(5) Solubility: soluble in aqueous solution at pH 7.0, aqueous sodium bicarbonate, diluted aqueous solutions of alkali hydroxides, methanol-water mixtures; partially soluble in methanol and ethanol; insoluble in diluted mineral acids and in non-polar organic solvents;

(6) Characteristic reactions:

| | | |
|---|---|---|
| Fehling | positive | |
| Tollens | positive | |
| KMnO4 | positive | |
| FeCl3 | positive | |
| H2SO4 concentrated | dark violet color | |
| Folin Ciocolteu | positive | |
| Griess | negative | |
| Antrone | negative | |
| Schiff | negative; | |

(7) Potentiometric titrations: an ionizable function is potentiometrically evidenced in water solutions with a pKa value=4.9; a basic function is evidenced by titration with HClO4 in DMSO solutions; the equivalent weight determined accordingly is 1170;

(8) Chromatographic pattern:
(a) on Whatman Paper No. 1, a cotton fibre cellulose filter paper with the following characteristics; weight, 85–95 g/m$^2$; thickness, 0.16 mm; ash content, 0.06–0.07%:

| | ELUTING SYSTEM | Rf |
|---|---|---|
| (1) | Butanol saturated with phosphate buffer m/15 pH 6.0 | 0.0 |
| (2) | Butanol saturated with water containing 2% of p-toluenesulfonic acid | 0.13 |
| (3) | Butanol saturated with water containing 2% ammonium hydroxide | 0.0 |
| (4) | Phosphate buffer M/15 pH 6.0 saturated with butanol | 0.25 |
| (5) | 20% Aqueous solution of NH4Cl | 0.0 |
| (6) | Butanol:methanol:water (40:10:20) with 0.75% of methyl orange | 0.37 |
| (7) | Butanol:methanol:water (40:10:20) | 0.41 |
| (8) | Ethyl acetate saturated with water | 0.0 |
| (9) | n-propanol:n-butanol:NH4OH 10 N (2:3:4) | 0.43 |

(b) on silica gel thin layer

| ELUTING SYSTEM | Rf |
|---|---|
| n-propanol:ethyl acetate: concentrated NH4OH (2:1:2) | 0.1. |

2. The antibiotic substance named teichomycin A1 having the following characteristics:
(1) Melting point: 220° C. (with decomposition);
(2) Elemental analysis (average of three determinations): C=59.9%; H=7.6%; N=5.26%; O=32.5%; P=0.96%, ash=2.30%;
(3) No U.V. absorption between 220 and 360 nm;
(4) I.R. absorption spectrum in nujol mull (FIG. 3): The most important absorption bands occur at the following frequencies (cm$^{-1}$); 3350 (broad), 2930–2850 (nujol), 2750–2000, 1720 (shoulder), 1670 (broad), 1620 (shoulder), 1560 (broad), 1460 and 1370 (nujol), 1340 (shoulder) 1260, 1240, 1155 (shoulder), 1120 (shoulder), 1040 (very broad), 970 (broad), 950 (shoulder), 900 (broad) 865, 805, 720;
(5) Solubility: soluble in aqueous solution at pH 7.0, aqueous sodium bicarbonate, diluted aqueous solutions of alkali hydroxides, dimethylformamide, dimethylsulfoxide; partially soluble in methanol and ethanol; insoluble in diluted mineral acids and in non-polar organic solvents;

(6) Characteristic reactions:

| Fehling | positive |
|---|---|
| Tollens | positive |
| KMnO4 | positive |
| Griess | negative |
| Antrone | positive |
| Schiff | negative |
| Molish | positive; |

(7) Molecular weight: Determinations of molecular weight by chromatography through a cross-linked polydextran gel with a range of fractionation, expressed in molecular weight, between 3,000 and 70,000 and a dry bead diameter of between 40 and 120 microns, show the following values: 20,000 in phosphate buffer pH 7.38, 30,000 in citrate buffer pH 4.4;

(8) Chromatographic pattern:
(a) on Whatman Paper No. 1, a cotton fibre cellulose filter paper with the following characteristics: weight 85–95 g/m$^2$; thickness, 0.16 mm; ash content, 0.06–0.07%.

| | ELUTING SYSTEM | Rf |
|---|---|---|
| (1) | Butanol saturated with phosphate buffer M/15 pH 6.0 | 0.0 |
| (2) | Butanol saturated with water containing 2% of p-toluenesulfonic acid | 0.05 |
| (3) | Butanol saturated with water containing 2% ammonium hydroxide | 0.0 |
| (4) | Phosphate buffer M/15 pH 6.0 saturated with butanol | 0.20 |
| (5) | 20% Aqueous solution of NH4Cl | 0.0 |
| (6) | Butanol:methanol:water (40:10:20) with 0.75% of methyl orange | 0.42 |
| (7) | Butanol:methanol:water (40:10:20) | 0.46 |
| (8) | Ethyl acetate saturated with water | 0.0 |
| (9) | n-propanol:n-butanol:NH4OH N (2:3:4) | 0.55 |

(b) on silical gel thin layer

| ELUTING SYSTEM | Rf |
|---|---|
| n-propanol:ethyl acetate:concentrated NH4OH (2:1:2) | 0.48. |

3. A process for producing antibiotic substances named teichomycin A2 and teichomycin A1 which comprises cultivating the strain *Actinoplanes teichomyceticus nov. sp.* ATCC 31121 under aerobic conditions in an aqueous nutrient medium containing an assimilable source of carbon, an assimilable source of nitrogen, and inorganic salts until a substantial antibiotic activity, which contains antibiotic substances including teichomycin A2 and teichomycin A1, is present in the medium, filtering the said medium and recovering said teichomycins A2 and A1 by extracting the resultant filtrate with an organic solvent in which the said teichomycins are soluble and which is immiscible with the remainder of the aqueous filtrate, the aqueous filtrate having first been adjusted to a pH of about 3.5, separating the solvent extract from the aqueous filtrate, concentrating the solvent extract under vacuum to give a precipitate on cooling to about 4° C., filtering off the precipitate and individually separating from the precipitate the two antibiotic substances teichomycin A2 and teichomycin A₁ by column chromatography on a hydroxypropyl derivative of a cross-linked polydextran gel with an exclusion limit at about molecular weight 4,000 and a dry bead diameter of between 25 and 100 microns, using a mixture of n-propanol:ethyl acetate:NH₄OH 0.2 N 10:7:7 as eluent, said teichomycins A₂ and A₁ having the following characteristics:

Teichomycin A₂:

(1) Melting point: 260° C. (with decomposition);
(2) Elemental analysis (average of three determinations): C=54.20%; H=5.70%; N=6.80%; Cl=3.30%; O (by difference)=30%;
(3) Ultraviolet absorption spectrum (FIG. 1):

| Solvent | $\lambda_{max}$ (nm) | $E^{1\%}{}_{1cm}$ |
|---|---|---|
| phosphate buffer pH 7.38 | 278 | 55 |
| hydrochloric acid 0.1 N | 278 | 53 |
| sodium hydroxide 0.1 N | 297 | 74; |

(4) I.R. absorption spectrum in nujol mull (FIG. 2): The most important absorption bands occur at the following frequencies (cm⁻¹): 3300 (broad), ~2900 (nujol), 1720 (shoulder), 1660, 1600 (shoulder), ~1500, 1455 (nujol), 1375 (nujol), 1235, 1190–930, 850 720 (broad);
(5) Solubility: soluble in aqueous solution at pH 7.0, aqueous sodium bicarbonate, diluted aqueous solutions of alkali hyhdroxides, methanol-water mixtures; partially soluble in methanol and ethanol; insoluble in diluted mineral acids and in non-polar organic solvents;
(6) Characteristic reactions:

| Fehling | positive |
|---|---|
| Tollens | positive |
| KMnO₄ | positive |
| FeCl₃ | positive |
| H₂SO₄ concentrated | dark violet color |
| Folin Ciocolteu | positive |
| Griess | negative |
| Antrone | negative |
| Schiff | negative; |

(7) Potentiometric titrations: an ionizable function is potentiometrically evidenced in water solutions with a pKa value=4.9; a basic function is evidenced by titration with HClO₄ in DMSO solutions; the equivalent weight determined accordingly is 1170;
(8) Chromatographic pattern:
(a) on Whatman Paper No. 1, a cotton fibre cellulose filter paper with the following characteristics; weight, 85–95 g/m²; thickness, 0.16 mm; ash content, 0.06–0.07%:

| | ELUTING SYSTEM | Rf |
|---|---|---|
| (1) | Butanol saturated with phosphate buffer m/15 pH 6.0 | 0.0 |
| (2) | Butanol saturated with water containing 2% of p-toluenesulfonic acid | 0.13 |
| (3) | Butanol saturated with water containing 2% ammonium hydroxide | 0.0 |
| (4) | Phosphate buffer M/15 pH 6.0 saturated with butanol | 0.25 |
| (5) | 20% Aqueous solution of NH₄Cl | 0.0 |
| (6) | Butanol:methanol:water (40:10:20) with 0.75% of methyl orange | 0.37 |
| (7) | Butanol:methanol:water (40:10:20) | 0.41 |

-continued

| | ELUTING SYSTEM | Rf |
|---|---|---|
| (8) | Ethyl acetate saturated with water | 0.0 |
| (9) | n-propanol:n-butanol:NH₄OH 10 N (2:3:4) | 0.43 |

(b) on silica gel thin layer

| ELUTING SYSTEM | Rf |
|---|---|
| n-propanol:ethyl acetate:concentrated NH₄OH (2:1:2) | 0.1; |

Teichomycin A₁:

(1) Melting point: 220° C. (with decomposition);
(2) Elemental analysis (average of three determinations): C=59.9%; H=7.6%; N=5.26%; O=32.5%; P=0.96%; ash=2.30%;
(3) No U.V. absorption between 220 and 360 nm;
(4) I.R. absorption spectrum in nujol mull (FIG. 3): The most important absorption bands occur at the following frequencies (cm⁻¹): 3350 (broad), 2930–2850 (nujol), 2750–2000, 1720 (shoulder), 1670 (broad), 1620 (shoulder), 1560 (broad), 1460 and 1370 (nujol), 1340 (shoulder) 1260, 1240, 1155 (shoulder), 1120 (shoulder), 1040 (very broad), 970 (broad), 950 (shoulder), 900 (broad) 865, 805, 720;
(5) Solubility: soluble in aqueous solution at pH 7.0, aqueous sodium bicarbonate, diluted aqueous solutions of alkali hydroxides, dimethylformaide, dimethylsulfoxide; partially soluble in methanol and ethanol; insoluble in diluted mineral acids and in non-polar organic solvents;
(6) Characteristic reactions:

| Fehling | positive |
|---|---|
| Tollens | positive |
| KMnO₄ | positive |
| Griess | negative |
| Antrone | positive |
| Schiff | negative |
| Molish | positive; |

(7) Molecular weight: Determinations of molecular weight by chromatography through a cross-linked polydextran gel with a range of fractionation, expressed in molecular weight, between 3,000 and 70,000 and a dry bead diameter of between 40 and 120 microns, show the following values: 20,000 in phsophate buffer pH 7.38, 30,000 in citrate buffer pH 4.4;
(8) Chromatographic pattern:
(a) on Whatman Paper No. 1, a cotton fibre cellulose filter paper with the following characteristics: weight 85–95 g/m²; thickness, 0.16 mm; ash content, 0.06–0.07%:

| | ELUTING SYSTEM | Rf |
|---|---|---|
| (1) | Butanol saturated with phosphate buffer M/15 pH 6.0 | 0.0 |
| (2) | Butanol saturated with water containing 2% of p-toluenesulfonic acid | 0.05 |
| (3) | Butanol saturated with water containing 2% ammonium hydroxide | 0.0 |
| (4) | Phosphate buffer M/15 pH | |

| ELUTING SYSTEM | Rf |
|---|---|
| 6.0 saturated with butanol | 0.20 |
| (5) 20% Aqueous solution of NH₄Cl | 0.0 |
| (6) Butanol:methanol:water (40:10:20) with 0.75% of methyl orange | 0.42 |
| (7) Butanol:methanol:water (40:10:20) | 0.46 |
| (8) Ethyl acetate saturated with water | 0.0 |
| (9) n-propanol:n-butanol: NH₄OH N (2:3:4) | 0.55 |

(b) on silical gel thin layer

| ELUTING SYSTEM | Rf |
|---|---|
| n-propanol:ethyl acetate:concentrated NH₄OH (2:1:2) | 0.48. |

4. The process of claim 3 wherein the cultivation is carried out at a temperature between about 25° C. and about 35° C.

5. The process of claim 3 wherein the cultivation is carried out for a time ranging from about 72 to about 120 hours.

6. The process of claim 3 wherein the antibiotic activity resulting from the cultivation is recovered by extraction with a halogenated $C_1$–$C_4$ hydrocarbon or $C_4$–$C_6$ alkanol.

7. The process of claim 6 wherein the extraction is made with butanol.

* * * * *